(12) United States Patent  (10) Patent No.: US 8,818,528 B2
Satake et al.  (45) Date of Patent: Aug. 26, 2014

(54) INTERNAL PADDLE ELECTRODE

(75) Inventors: Katsunori Satake, Tokyo (JP); Koji Ishino, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 279 days.

(21) Appl. No.: 12/834,039

(22) Filed: Jul. 12, 2010

(65) Prior Publication Data

US 2011/0009936 A1    Jan. 13, 2011

(30) Foreign Application Priority Data

Jul. 13, 2009 (JP) ................................. 2009-165157

(51) Int. Cl.
*A61N 1/00* (2006.01)

(52) U.S. Cl.
USPC ........... 607/119; 607/129; 607/145; 607/149; 607/150

(58) Field of Classification Search
CPC ............................ A61N 1/0587; A61N 1/3968
USPC .................................. 607/119, 129–131, 145
See application file for complete search history.

(56) References Cited

U.S. PATENT DOCUMENTS

| 4,567,900 A | | 2/1986 | Moore | |
|---|---|---|---|---|
| 4,920,978 A | * | 5/1990 | Colvin | 607/102 |
| 5,213,113 A | * | 5/1993 | Hlinsky | 607/152 |
| 6,068,647 A | * | 5/2000 | Witt et al. | 606/205 |
| 6,584,360 B2 | * | 6/2003 | Francischelli et al. | 607/98 |
| 2006/0116746 A1 | | 6/2006 | Chin | |

FOREIGN PATENT DOCUMENTS

| JP | 5-337193 A | 12/1993 |
|---|---|---|
| JP | 11-47155 A | 2/1999 |

OTHER PUBLICATIONS

Extended European Search Report issued in corresponding Application No. 10169219.2, dated Nov. 24, 2010.
Office Action dated Nov. 1, 2011 from the Japanese Patent Office in counterpart Japanese application No. 2009-165157.

* cited by examiner

*Primary Examiner* — Michael Kahelin
*Assistant Examiner* — Mallika D Fairchild
(74) *Attorney, Agent, or Firm* — Sughrue Mion, PLLC

(57) ABSTRACT

An internal paddle electrode includes: an electrode which is to be in contact with a living body to apply a voltage; a cable which includes a voltage supply path that extends between a voltage supply source and the electrode; a handle which includes: a first portion that supports the electrode and is hermetically sealed with the electrode; and a second portion that is connected to the cable and is hermetically sealed with the cable; and a gas passage through which a gas in the handle communicates with external air that is outside the handle.

4 Claims, 5 Drawing Sheets

INTERNAL PADDLE ELECTRODE

BACKGROUND OF THE INVENTION

The present invention relates to an internal paddle electrode having an electrode which is to be in direct contact with the heart (living body) of the patient.

An internal paddle electrode of this kind is used in the following manner. The heart of the patient is interposed between a pair of electrodes, and a voltage from a defibrillator is applied to the heart. A known internal paddle electrode is of a type in which an electrode can be separated from a handle. The internal paddle electrode is configured so that the handle can withstand sterilization (see JP-A-5-337193, particularly see paragraph 0027).

On the other hand, there is also an internal paddle electrode of a type in which an electrode cannot be separated from a handle. The handle is required to be washed and sterilized by flowing water or the like. However, the electrode and the handle do not have a hermetically sealed structure. When washed with flowing water, therefore, blood and the like penetrate through a gap between the electrode and the handle, and hence blood and the like are wiped off with a cloth or the like.

After wiping, the internal paddle electrode is sterilized in the following manner. A sterilizing process which is called autoclave, and in which a process where sterilization is performed at a pressure of about 2 atm. and a high temperature of 130 degrees Celsius for about 10 to 20 minutes, and thereafter the normal pressure is introduced by reducing the pressure is repeated. In the case where the electrode and the handle have a hermetically sealed structure, washing with flowing water is enabled, but, when autoclave sterilization is performed, the internal pressure of the handle becomes higher than the external pressure because the handle has a hermetically sealed structure. Therefore, there arises a problem in that a cover covering the outside of the handle is expanded to be deformed.

SUMMARY

It is therefore an object of the invention to provide an internal paddle electrode in which a handle can be washed with flowing water or the like, and, even when autoclave sterilization is performed, a cover is not deformed by expansion.

In order to achieve the object, according to the invention, there is provided an internal paddle electrode comprising:
an electrode which is to be in contact with a living body to apply a voltage;
a cable which includes a voltage supply path that extends between a voltage supply source and the electrode;
a handle which includes:
a first portion that supports the electrode and is hermetically sealed with the electrode; and
a second portion that is connected to the cable and is hermetically sealed with the cable; and
a gas passage through which a gas in the handle communicates with external air that is outside the handle.

The gas passage may be provided in the cable.

The gas passage in the cable may have a block preventing structure.

A communication opening portion of the gas passage which is exposed to the external air may be provided in a connecting portion where the cable is to be connected to the voltage supply source.

The handle may include: a shaft portion that is connected to the electrode; and a grip portion that is symmetrical about the shaft portion.

A plurality of the gas passage may be provided in the cable.

DETAILED DESCRIPTION OF EMBODIMENTS

Figure 1:
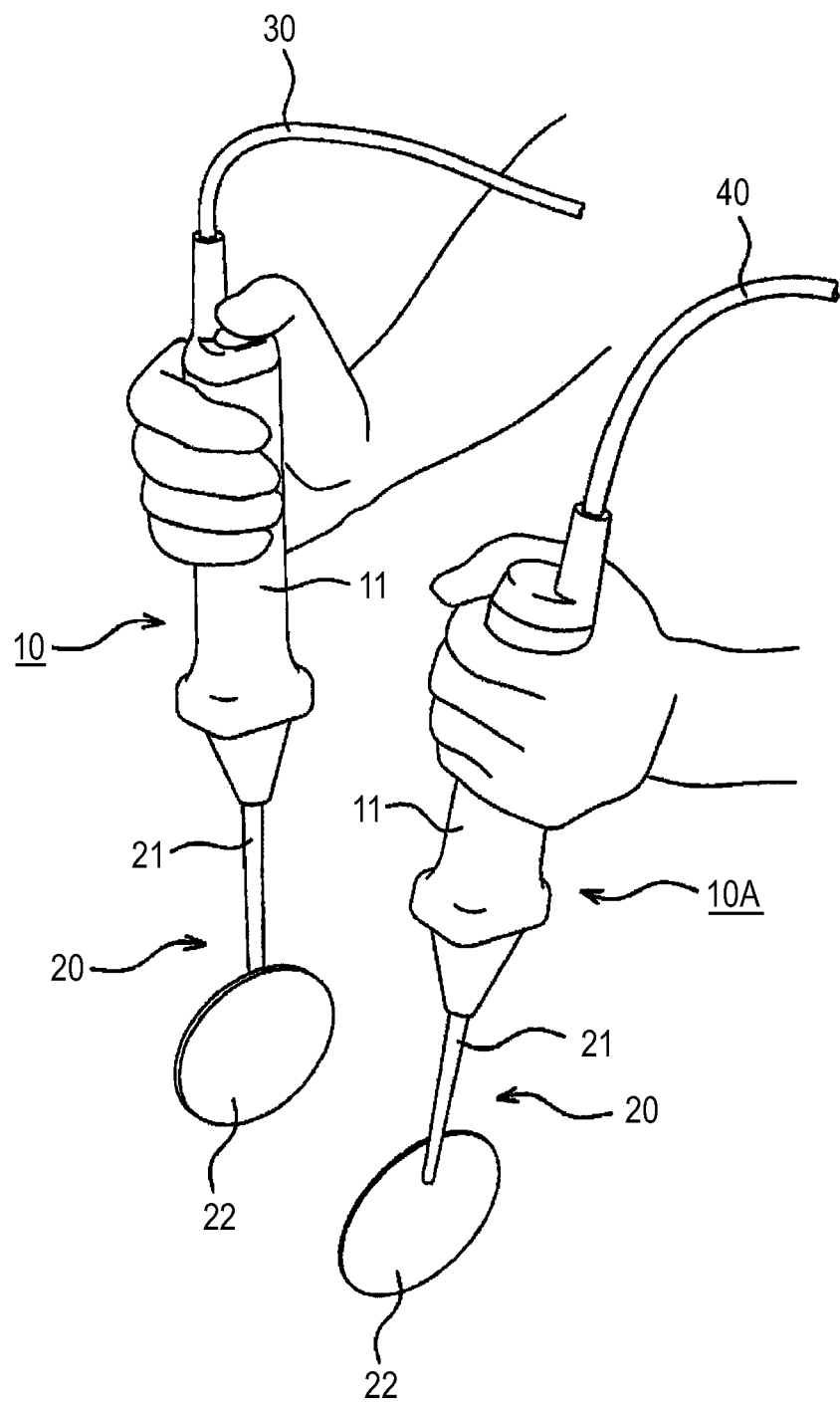
FIG. 1 is a view showing a use state of an internal paddle electrode of an embodiment of the invention.
Figure 2:
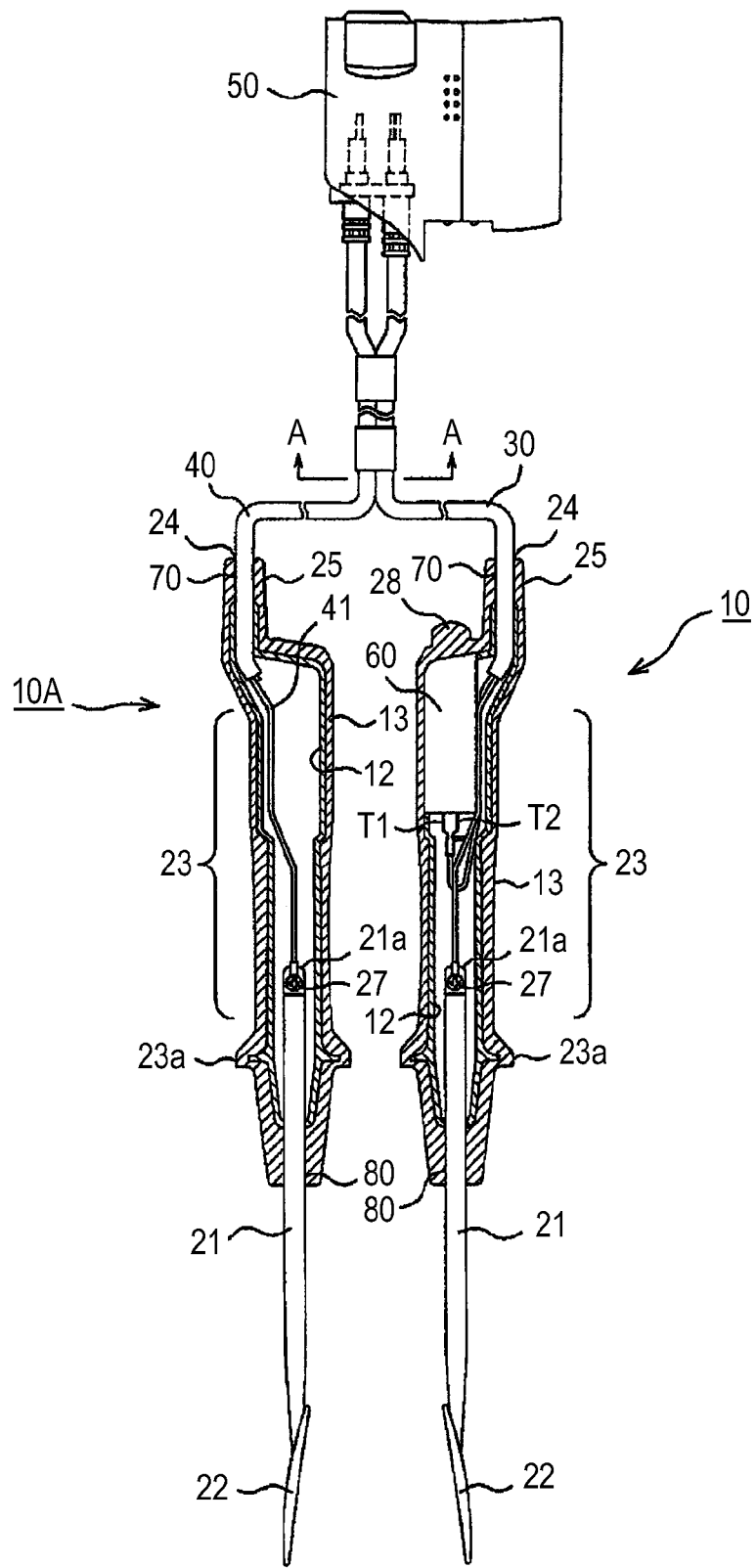
FIG. 2 is a longitudinal sectional view of the internal paddle electrode of FIG. 1.
Figure 3:
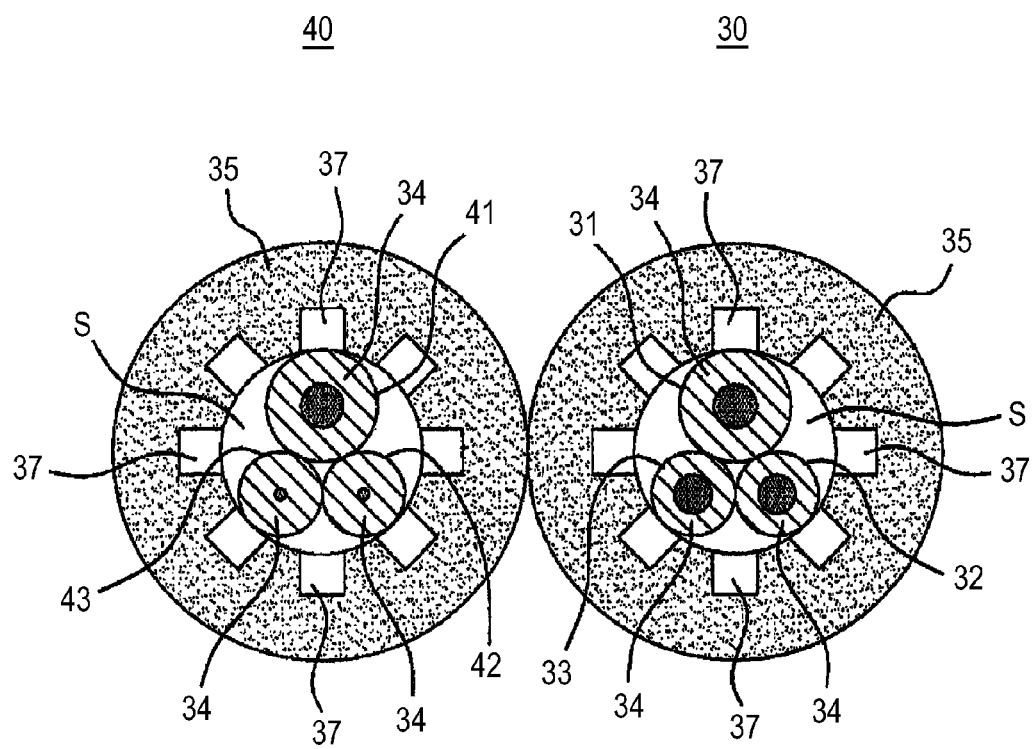
FIG. 3 is a sectional view taken along A-A in FIG. 2.

Hereinafter, an embodiment of the internal paddle electrode of the invention will be described with reference to the accompanying drawings. In the figures, identical components are denoted by the same reference numerals, and duplicated description will be omitted. FIG. 1 is a perspective view showing a use state of an internal paddle electrode of the embodiment of the invention, FIG. 2 is a sectional view in which the section line extends substantially in the longitudinal direction in FIG. 1, and FIG. 3 is a sectional view taken along A-A in FIG. 2. The internal paddle electrode of the embodiment is used in the form of a pair of a first paddle 10 having a switch and a second switch 10A having no switch.

In each of the first and second paddles 10, 10A, an electrode 20 is disposed on one end side of a handle 11, and a cable 30 or 40 extends from the other end side of the handle 11 so as to be connectable to a defibrillator which is not shown.

The electrode 20 includes a shaft portion 21, and a disk electrode portion 22 which is disposed on the tip end side of the shaft portion 21, and which has a disk-like shape. The shaft portion 21 is made of a highly electrically conductive material which has a columnar shape, and which is tapered toward the disk electrode portion 22. A part of the shaft portion 21 which is located on the side of the disk electrode portion 22 is exposed from the handle 11.

The handle 11 includes an inner case 12 which is made of a hard insulative resin or the like, and a cover 13 which covers the inner case 12, and which is made of an outer molding material such as a soft insulative resin. Alternatively, the inner case 12 and the cover 13 may be configured so that they are integral with each other and made of the same material. The handle 11 has a hollow cylindrical shape. A stopper 23a which is outward protruded so as to extend around the diameter of the handle 11 is formed in a portion of the end of the handle 11 on the side where the shaft portion 21 is protruded. The handle 11 is tapered from the stopper 23a toward the shaft portion 21.

The handle 11 has a hollow cylindrical grip portion 23 which elongates from the stopper 23a in the direction opposite to the shaft portion 21 with a substantially same diameter, and which has a shape that is easy to hold with the hand. A sleeve 25 having a through hole 24 through which the cable 30 or 40 enters into the handle 11 is formed curvedly and squeezedly from the grip portion 23 toward an end portion.

In the first paddle 10, a key-top cover portion 28 having a convex shape is formed by the cover 13 in an end portion of the grip portion 23 in the vicinity of the sleeve 25. In a predetermined length portion which is continuous from the key-top cover portion 28 toward the stopper 23a, the inner case 12 does not exist, and a switch chassis 60 which is in contact with the cover 13 is placed. A key of the switch chassis 60 is in contact with the key-top cover portion 28.

Figure 4:
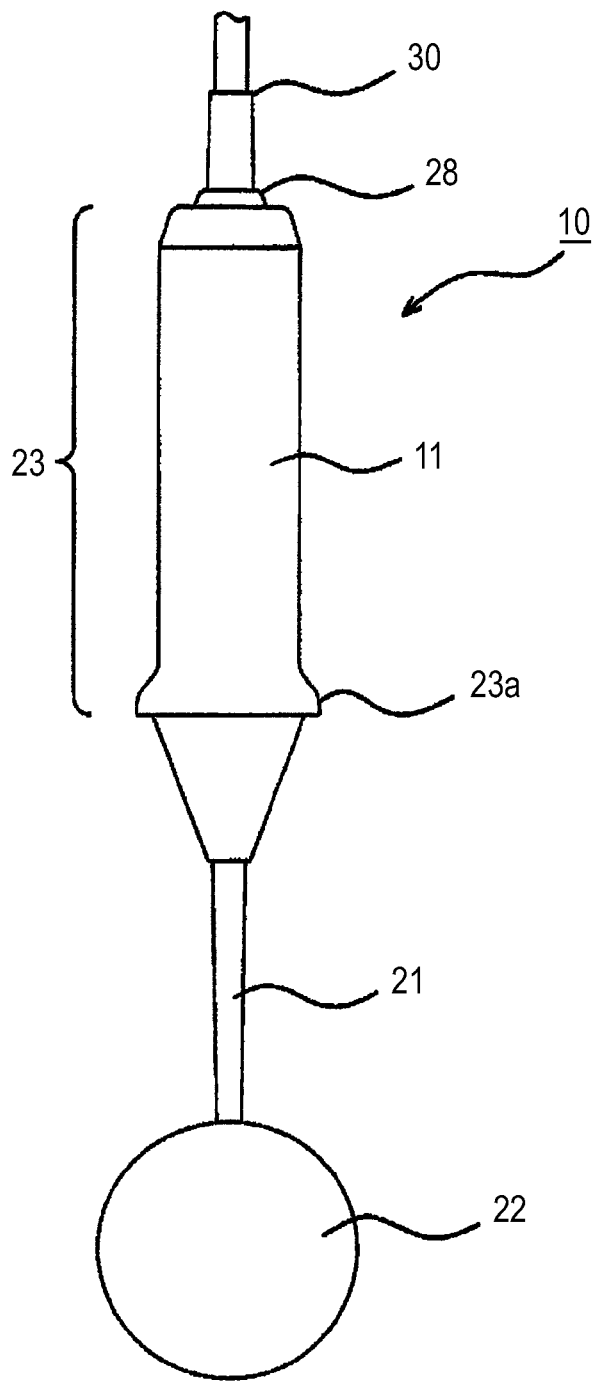
FIG. 4 is a front view of the internal paddle electrode of FIG. 1.
Figure 5:
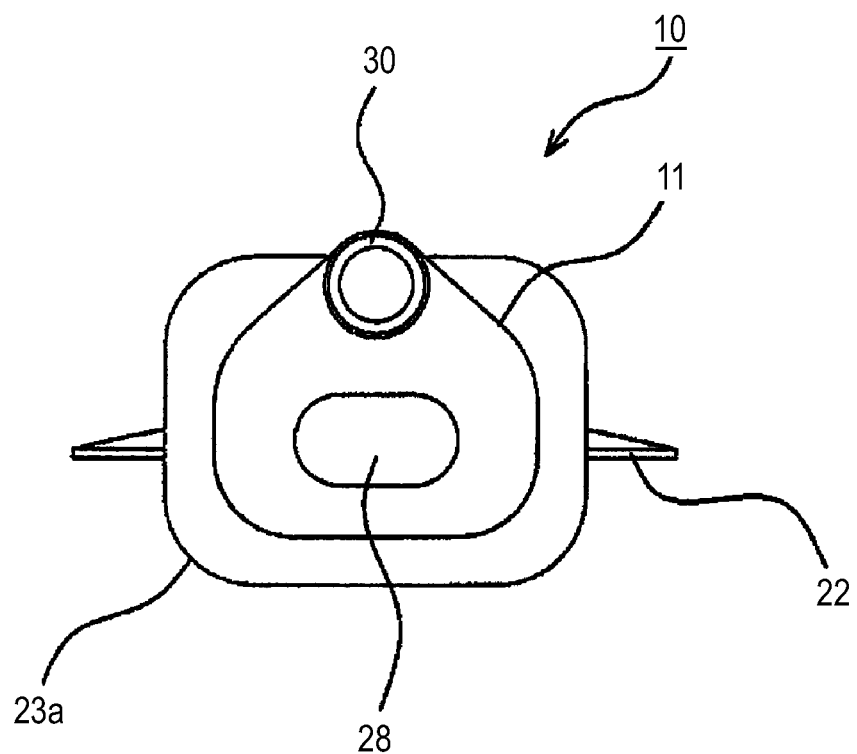
FIG. 5 is a plan view of the internal paddle electrode of FIG. 1.

As shown in FIGS. 4 and 5, the grip portion 23 and stopper 23a of the handle 11 are formed in a bilaterally symmetrical manner about the longitudinal axis of the shaft portion 21. Although, in FIGS. 4 and 5, the first paddle 10 is shown as an example, also the second paddle 10A having no switch is structured so that it is bilaterally symmetrical about the longitudinal axis of the shaft portion 21. Therefore, the embodiment has a feature that, irrespective of whether the user is right-handed or left-handed, the user can operate the switch while holding the first paddle 10 with the dominant hand.

As shown in FIG. 3, in the cable 30, a high-voltage line 31 and two signal lines 32, 33 are wired, and, in the cable 40, a high-voltage line 41 and two dummy lines 42, 43 are wired. Each of the core portions of the dummy lines 42, 43 is configured by a core of very thin fibers which are called Kevlar.

The outsides of the cores of the high-voltage lines 31, 41 and the signal lines 32, 33 and those of the dummy lines 42, 43 are covered by insulating members 34, respectively. The outermost shells of the cables 30, 40 are covered by shielding materials 35, respectively. In each of the cables 30, 40, a plurality of through holes 37 which are passed in the longitudinal direction of the cable 30 or 40, and which have an adequate section shape are formed. The plurality of through holes 37 configure a gas passage for communicating the gas existing in the inner case 12 of the handle 11 to the external air outside the handle 11. Since the plurality of through holes 37 exist, a block preventing structure which prevents the through holes 37 from being blocked even when the cable 30 or 40 is bent is formed. In the embodiment, also an air gap S which is formed between the shield material 35 and the insulating member 34 functions as a gas passage for communicating the gas existing in the inner case 12 of the handle 11 to the external air outside the handle 11.

The high-voltage line 31 of the cable 30 is wired through the interior of the handle 11, and coupled by a screw 27 to a screwing part 21a which is formed in the basal portion of the shaft portion 21. The two signal lines 32, 33 of the cable 30 are wired through the interior of the handle 11, and connected to terminals T1, T2 which are linked to switch contacts in the switch chassis 60, respectively. The high-voltage line 41 of the cable 40 is wired through the interior of the handle 11, and coupled by a screw 27 to a screwing part 21a which is formed in the basal portion of the shaft portion 21.

In the sleeve 25 of the cover, a part 70 which covers the cable 30 or 40, and a part 80 which supports the shaft portion 21 are configured to be watertight by means close contact. The handle 11 includes a case portion which incorporates the part 80 that supports the electrode 20 and the part 70 which is a joining portion that joins to the cable 30 or 40, in a hermetically sealed structure by means of fusion bonding.

The other ends of the cables 30, 40 are connected to a body unit-paddle connector 50 which is to be connected to a paddle connector of a defibrillator which constitutes the apparatus body unit functioning as a voltage supply source. As described above, in the plurality of through holes 37 configuring the gas passage, the communication opening portion with respect to the external air is formed in the connecting portion where the cables 30, 40 are connected to the defibrillator which is the apparatus body unit.

The thus configured internal paddle electrode is used in the following manner. The body unit-paddle connector 50 is connected to the paddle connector of the defibrillator. The power supply of the defibrillator is turned ON, an electrocardiogram lead is confirmed, and it is further confirmed that unsynchronized defibrillation mode is set. The heart is sandwiched between the disk electrode portions 22, 22 while supporting the first paddle 10 and the second paddle 10A, the output energy is set, and the energy is charged. Then, the key-top cover portion 28 is pressed to energize the electrodes. At this time, the switch can be operated while the first paddle 10 is held with the dominant hand, and therefore it is easy to manipulate. After use, the power supply is turned OFF, and the paddles are detached in the procedure reverse to the above-described one.

After the above-described process, washing and autoclave sterilization are performed. In this case, since, in the cover 13, the part 70 of the sleeve 25 which covers the cable 30 or 40, and the part 80 which covers the shaft portion 21 are configured to be watertight as described above, there is no possibility that liquids for washing and blood enter into the handle 11. Therefore, washing can be sufficiently performed.

The pressure of the interior of the handle 11 is increased during the autoclave sterilization. However, the gas existing in the inner case 12 of the handle 11 is discharged from the body unit-paddle connector 50 through the plurality of through holes 37 and the air gap S which is formed between the shield material 35 and the insulating member 34. Moreover, the block preventing structure in which the plurality of through holes 37 are formed is configured. Even when the cable 30 or 40 is bent during the autoclave sterilization, therefore, the gas passage is not blocked, so that the cover 13 is not deformed.

In the embodiment, the through holes 37 each functioning as a gas passage are formed in the shield material 35. Alternatively, another appropriate configuration such as that in which tubes are disposed in the cables 30 and 40 may be employed as far as a gas passage for communicating the gas existing in the inner case 12 of the handle 11 to the external air outside the handle 11 is formed.

According to an aspect of the invention, the handle can be washed because the interior is hermetically sealed, and, in the case of autoclave sterilization, the gas passage functions as a passage through which the gas in the handle escapes, so that, even when autoclave sterilization is performed, deformation of the handle due to expansion can be prevented from occurring.

According to an aspect of the invention, the gas passage is not blocked by kink of the cable, so that, when autoclave sterilization is performed, the gas in the handle can escape by using the cable.

According to an aspect of the invention, when autoclave sterilization is performed, the gas in the handle can be discharged while escaping to the vicinity of the apparatus body unit and it is possible to avoid the risk that blood, various solutions, and the like enter through the communication opening portion during surgery.

According to an aspect of the invention, it is possible to provide an internal paddle electrode which is easy to operate irrespective of whether the user is right-handed or left-handed.

What is claimed is:
1. An internal paddle electrode comprising:
an electrode which is configured to be in contact with a living body to apply a voltage;
a cable which is adapted to be connected to a voltage supply source and the electrode and which includes a line that is electrically connected to the voltage supply source and the electrode, and a shielding material that covers the line and defines an outermost shell of the cable, the shielding material which includes a plurality of through holes that extend along the line and that are formed at an inner wall portion of the shielding material;

a handle which includes:
   a first portion that supports the electrode and is hermetically sealed with the electrode; and
   a second portion that is connected to the cable and is hermetically sealed with the cable; and a gas passage which is disposed in the cable and which is adapted to communicate between a gas in the handle and external air that is outside the handle, the gas passage which is defined by the plurality of through holes and a gap that is formed between the line and the shielding material and that is surrounding by the plurality of through holes.

2. The internal paddle electrode according to claim 1, wherein the gas passage in the cable has a block preventing structure with the plurality of through holes.

3. The internal paddle electrode according to claim 1, further comprising a communication opening portion of the gas passage which is exposed to the external air, wherein the communication opening portion is provided in a connecting portion of the cable where the cable is adapted to be connected to the voltage supply source.

4. The internal paddle electrode according to claim 1, wherein
   the handle includes:
      a shaft portion that is connected to the electrode; and
      a grip portion that is symmetrical about the shaft portion.

* * * * *